United States Patent
Morin et al.

(10) Patent No.: US 8,957,382 B2
(45) Date of Patent: Feb. 17, 2015

(54) METHOD AND DEVICE FOR SLAVING THE ACTIVATION OF A SET OF INFRARED EMITTERS OF A SENSOR OF VENOUS NETWORKS TO THE PRESENCE OF A LIVING BODY

(75) Inventors: Aurélie Morin, Paris (FR); Matthieu Darbois, Paris (FR); Olivier Goudon, Paris (FR); Yannick Balzac, Paris (FR)

(73) Assignee: Morpho, Paris (FR)

( * ) Notice: Subject to any disclaimer, the term of this patent is extended or adjusted under 35 U.S.C. 154(b) by 25 days.

(21) Appl. No.: 13/503,948

(22) PCT Filed: Oct. 25, 2010

(86) PCT No.: PCT/EP2010/066071
§ 371 (c)(1),
(2), (4) Date: Jul. 16, 2012

(87) PCT Pub. No.: WO2011/051230
PCT Pub. Date: May 5, 2011

(65) Prior Publication Data
US 2012/0298871 A1    Nov. 29, 2012

(30) Foreign Application Priority Data
Oct. 26, 2009 (FR) ...................................... 0957479

(51) Int. Cl.
*G01J 5/02* (2006.01)
*G06K 9/00* (2006.01)
*A61B 5/02* (2006.01)
*A61B 5/117* (2006.01)
*A61B 5/1455* (2006.01)
(Continued)

(52) U.S. Cl.
CPC .......... *G06K 9/0004* (2013.01); *A61B 5/02007* (2013.01); *A61B 5/117* (2013.01); *A61B 5/1455* (2013.01); *A61B 5/489* (2013.01); *G06K 9/00033* (2013.01); *G06K 9/2027* (2013.01); *G06K 2009/0006* (2013.01); *G06K 2009/00932* (2013.01)
USPC ......................................................... 250/349

(58) Field of Classification Search
USPC .................................. 250/349; 382/128, 234
See application file for complete search history.

(56) References Cited

U.S. PATENT DOCUMENTS

| 3,970,990 A | 7/1976 | Carson |
| 4,547,898 A | 10/1985 | Tsikos |
| 6,334,065 B1 * | 12/2001 | Al-Ali et al. .................. 600/323 |

(Continued)

OTHER PUBLICATIONS

International Search Report for PCT/EP2010/066071 mailed Jan. 13, 2011.

(Continued)

*Primary Examiner* — David J Makiya
*Assistant Examiner* — Taeho Jo
(74) *Attorney, Agent, or Firm* — Nixon & Vanderhye, PC

(57) ABSTRACT

The present invention relates to a method for slaving the activation of a set of infrared emitters of a sensor of venous networks to the presence of a living body between this set and an image acquisition means of the sensor. The method is characterized in that each infrared emitter (E) is activated if the presence of a part of the living body (CV) is detected by at least one presence detector (DP) which is associated therewith and each infrared emitter (E) is deactivated as long as the presence of a part of the living body (CV) is not detected.

6 Claims, 4 Drawing Sheets

Figure 1:
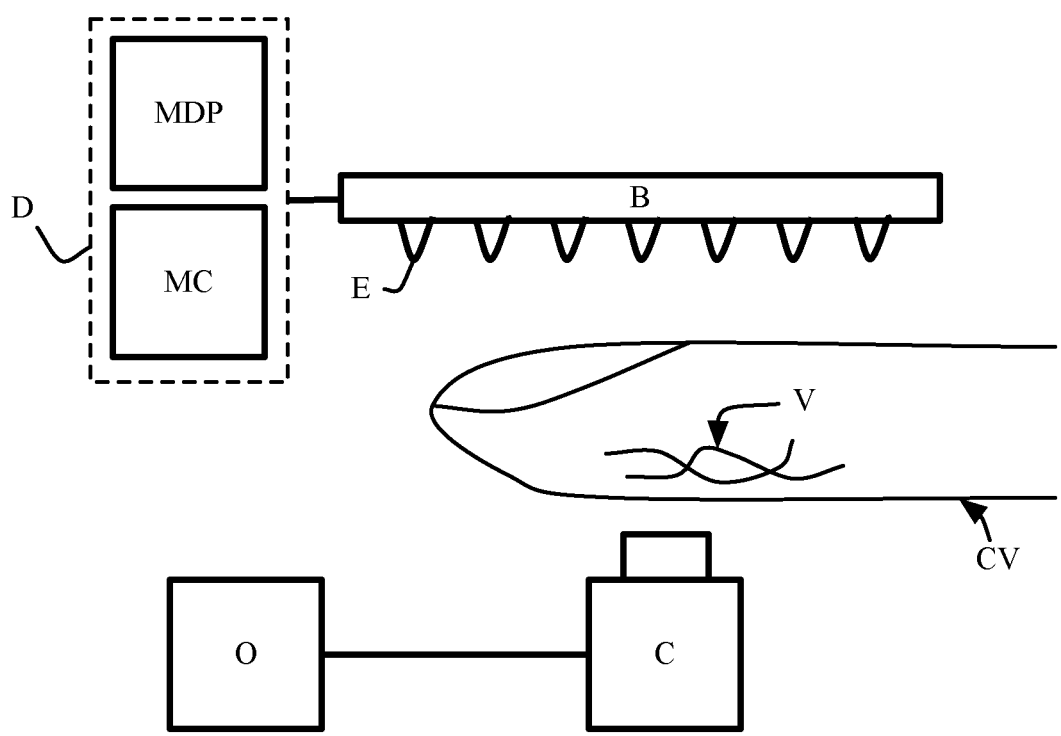

(51) Int. Cl.
*A61B 5/00* (2006.01)
*G06K 9/20* (2006.01)

(56) References Cited

U.S. PATENT DOCUMENTS

| | | | |
|---|---|---|---|
| 7,171,026 B2 * | 1/2007 | Shinada et al. | 382/104 |
| 7,620,212 B1 * | 11/2009 | Allen et al. | 382/115 |
| 8,284,019 B2 * | 10/2012 | Pishva | 340/5.2 |
| 8,417,959 B2 * | 4/2013 | Hill, Jr. | 713/182 |
| 8,489,178 B2 * | 7/2013 | Wood et al. | 600/473 |
| 2005/0047632 A1 * | 3/2005 | Miura et al. | 382/124 |
| 2005/0185847 A1 * | 8/2005 | Rowe | 382/224 |
| 2006/0002597 A1 * | 1/2006 | Rowe | 382/124 |
| 2006/0210120 A1 * | 9/2006 | Rowe et al. | 382/115 |
| 2007/0112259 A1 * | 5/2007 | Tateda et al. | 600/310 |
| 2008/0008365 A1 * | 1/2008 | Hikita et al. | 382/124 |
| 2008/0077200 A1 * | 3/2008 | Bendett et al. | 607/89 |
| 2008/0221426 A1 * | 9/2008 | Baker et al. | 600/407 |
| 2009/0060301 A1 * | 3/2009 | Carver et al. | 382/128 |
| 2009/0110249 A1 * | 4/2009 | Miura et al. | 382/124 |
| 2009/0245591 A1 * | 10/2009 | Rowe et al. | 382/115 |

OTHER PUBLICATIONS

Written Opinion of the International Searching Authority (foreign language) mailed Jan. 13, 2011.

M. Watanabe, "Palm Vein Authentication", In: N. Ratha and V. Govindaraju (Eds), Advances in Biometrics, 2008, XP-002615593, 6 pages.

International Preliminary report on Patentability in English for PCT/EP2010/066071, dated May 10, 2012.

* cited by examiner

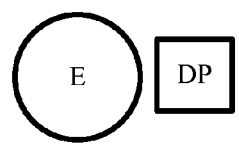
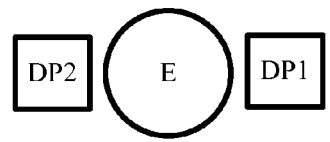
Fig. 2a  Fig. 2b
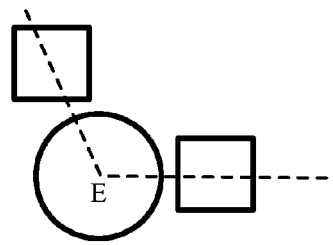
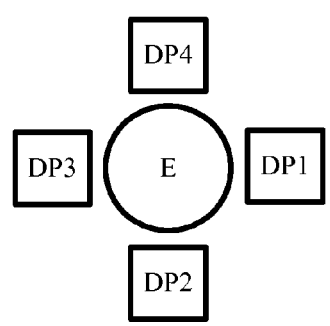
Fig. 2c  Fig. 2d
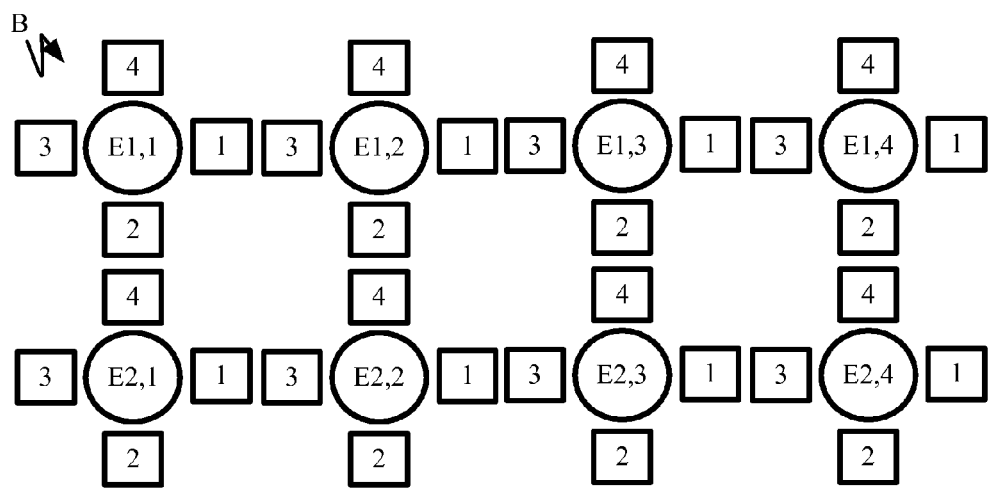
Fig. 3

METHOD AND DEVICE FOR SLAVING THE ACTIVATION OF A SET OF INFRARED EMITTERS OF A SENSOR OF VENOUS NETWORKS TO THE PRESENCE OF A LIVING BODY

This application is the U.S. national phase of International Application No. PCT/EP2010/066071 filed 25 Oct. 2010 which designated the U.S. and claims priority to FR 0957479 filed 26 Oct. 2009, the entire contents of each of which are hereby incorporated by reference.

The present invention concerns a method and device for slaving the activation of a set of infrared emitters of a sensor of venous networks to the presence of a living body.

A sensor of venous networks of a living body such as that of a finger, a hand, a toe, etc. is very much used, for example for controlling access to a site or a machine based on biometric data. For example, in the case of a fingerprint access control system, a venous network sensor is associated with a fingerprint sensor in order to increase the reliability of the access control system since it ensures that the fingerprint acquired does indeed come from a living finger and authenticates a user by comparing his fingerprint and a venous network of his finger with previously recorded biometric data.

A venous network sensor comprises an infrared source that illuminates an image acquisition means of the sensor, such as for example a CCD camera.

This infrared source is produced by a set of infrared emitters that are normally positioned with respect to one another in rows and/or columns. Arrays or matrices of infrared emitters are then spoken of.

When a living body is placed between the infrared source and the image acquisition means, some rays in the light flux strike the image acquisition means directly and others strike this means once they have passed through the living body. The image thus acquired is then processed digitally so that the venous networks of the living body appear on this image. A user can then be authenticated by comparing the venous network thus acquired and the venous network that he previously recorded.

Though the principle of a venous network sensor is simple, the use thereof poses the problem of over-exposure of the image acquired. This is because the rays that directly strike the image acquisition means induce an intensity of the pixels of the image that is high compared with that induced by the rays that pass through the living body. This difference in intensity causes artefacts on the acquired image, such as a light halo or local over-intensities, especially at the edges of the living body. These artefacts interfere with the processing operations that are applied to the acquired image in order to reveal the venous network.

In order to improve the quality of the acquisition of the venous network, venous network sensors comprise means for slaving the activation of all the infrared emitters to the presence of a living body. Thus, when part of the living body is present between one of the infrared emitters and the image acquisition means, this infrared emitter is activated and, when an infrared emitter directly illuminates the acquisition means, then this infrared emitter is deactivated.

It is known that such slaving means are used by image processing.

In particular, the patent US 2002048014 A1 describes a slaving method that consists firstly of weakly activating all the infrared emitters in the set when a living body is present. An image is then acquired by the image acquisition means and the position of the living body in the image is detected by processing the image thus acquired. The intensity of the pixels in the image is then considered and compared with a reference value. When the intensity of a pixel of the image is less than this reference value, the activation of the infrared emitter that induced the intensity of this pixel is increased so that the venous network can be extracted from a future image acquisition. On the other hand, when the intensity of a pixel of the image is higher than this reference value, the infrared emitter that induced the intensity of this pixel is deactivated.

Thus, by analysing the intensities of an image acquired when the infrared emitters are weakly activated, it is determined which of these infrared emitters must be strongly activated and which must be deactivated. When the living body moves, a new image is then acquired in order to determine once again which of the infrared emitters must be activated strongly and which must be deactivated. The activation (and deactivation) of the infrared emitters is thus slaved to the presence of a living body between the set of infrared emitters and the image acquisition means.

Once the finger is positioned in a stable fashion, that is to say the infrared emitters remain in a stable state (strongly activated or deactivated) for a period of time, a new image is acquired and the venous network is then extracted from this new image.

Such a method of slaving by analysing the intensities of an acquired image has several drawbacks.

First of all it is necessary to calibrate the image acquisition means in order to know the positions of the infrared emitters in the plane of the image. In other words, this slaving method requires that the infrared emitter that is inducing the intensity of each pixel in the image be known in advance. This constraint in use is all the more amplified when the sensor is calibrated during its manufacture since the relative positions of all the infrared emitters and of the image acquisition means must remain fixed for the slaving method to continue to function correctly. This involves either mechanical constraints at the venous network sensor, or providing a calibration phase before any use of the sensor.

Next, this slaving method will not be operational when the living body moves quickly. This is because, for the venous network to be able to be extracted from an acquired image, it is necessary first for another image to be acquired for the activation/deactivation of the infrared emitters. The slaving method by analysis of the intensities of an acquired image is therefore not suited to the acquisition of a venous network on the fly since an incompressible and automatic processing time takes place between the current position of the living body and the acquisition of the image from which the venous network will be extracted.

The problem addressed by the present invention is to remedy the drawbacks of the slaving methods of the prior art.

To this end, the present invention concerns a method for slaving the activation of a set of infrared emitters of a venous network sensor to the presence of a living body between this set and a means of acquiring images from the sensor. The method is characterised in that each infrared emitter is activated if the presence of a part of the living body is detected by at least one presence detector that is associated therewith and each infrared emitter is deactivated as long as the presence of a part of the living body is not detected.

The association of at least one presence detector with each of the infrared emitters in the set dissociates the slaving method from the image acquisition means and therefore avoids having to acquire an image in order to decide on the activation or deactivation of each infrared emitter.

A venous network sensor implementing such a method can then be used for acquiring a venous network on the fly since the delay inherent in the slaving method of the prior art no longer exists.

In addition, this dissociation of the method and acquisition means avoids using a prior calibration phase, thus facilitating the manufacture of the sensor and as well as use thereof.

The present invention also concerns a set of infrared emitters designed to illuminate an acquisition means of a venous network sensor. This set is characterised in that it comprises at least one presence detector associated with each infrared emitter.

According to one embodiment, four presence detectors are associated with each infrared emitter in the set, each of these four presence detectors being positioned at a cardinal point of each infrared emitter.

This particular positioning of the presence detectors avoids the movement of the living body being guided in order to be detected.

According to one embodiment, each infrared emitter and each presence detector in the set are positioned in at least one row and/or in at least one column, an infrared emitter alternating with a presence detector on each row and/or on each column.

The present invention also concerns a device for slaving the activation of a set of infrared emitters as above and comprises means for activating an infrared emitter if the presence of a part of the living body is detected by at least one presence detector that is associated with this infrared emitter, and for deactivating an infrared emitter as long as the presence of a part of the living body is not detected.

Finally, the present invention concerns a sensor of venous networks in a part of a living body comprising a set of infrared emitters and a device as above.

Figure 4A:
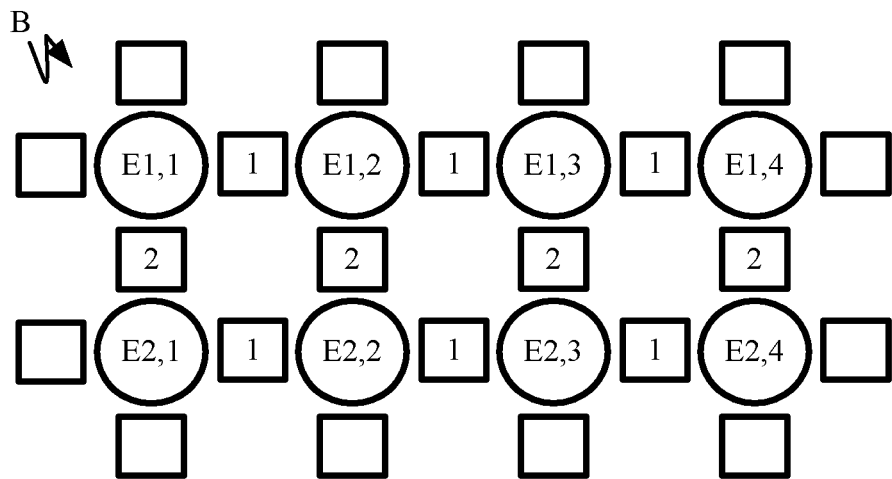
Figure 4B:
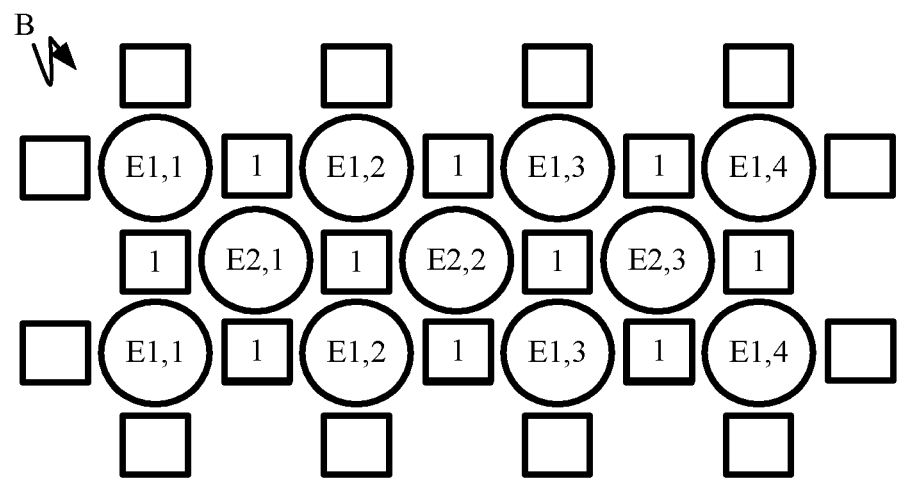
Figure 5:
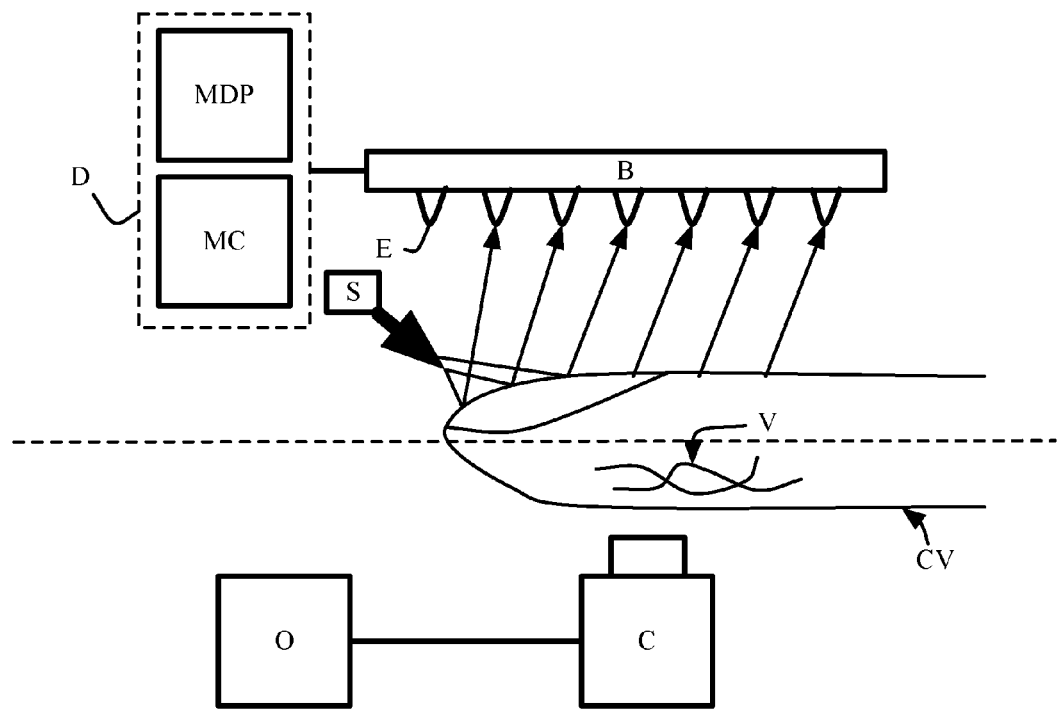
Figure 6:
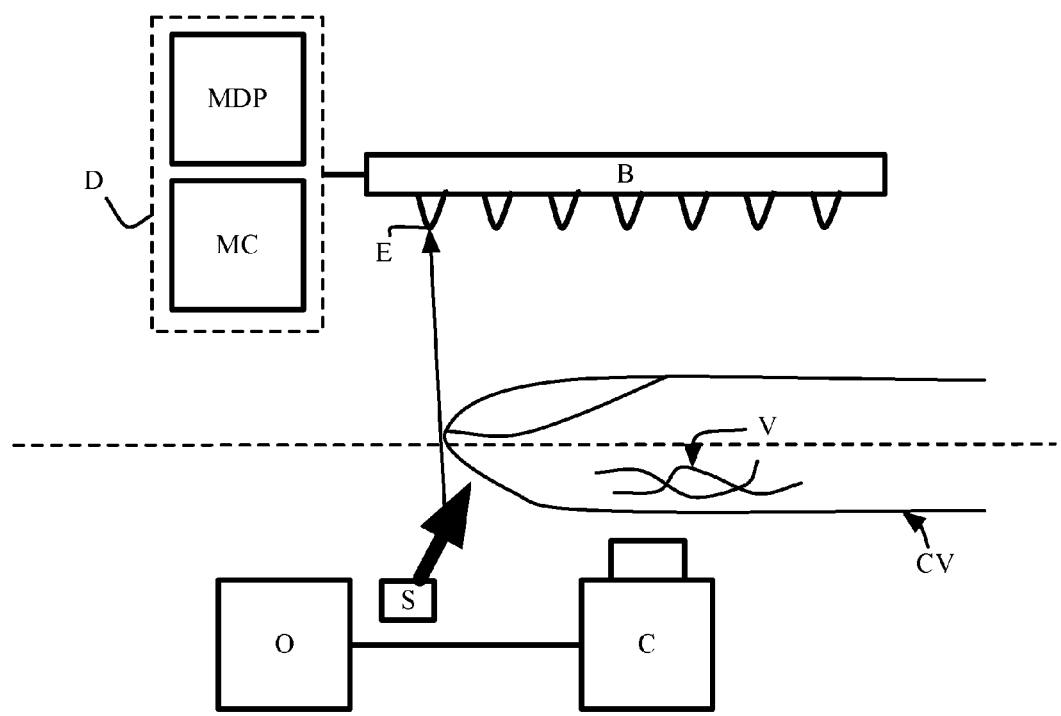

The features of the invention mentioned above, as well as others, will emerge more clearly from a reading of the following description of an example embodiment, said description being given in relation to the accompanying drawings, among which:

FIG. 1 shows a diagram of a venous network sensor,

FIGS. 2a-2d show various examples of associations of presence detectors with an infrared emitter, FIG. 3 shows an example of positioning of the infrared emitters, FIG. 4a shows another example of positioning of the infrared emitters, FIG. 4b shows a preferred embodiment of positioning of the infrared emitters, FIG. 5 shows an embodiment of the positioning of a light source in the venous network sensor, and FIG. 6 shows another embodiment of the positioning of a light source in the venous network sensor.

FIG. 1 shows schematically an example of a venous network sensor designed to acquire an image of the venous network V of a finger CV. It will be understood that this sensor is only one example embodiment, which can be adapted in particular for acquiring a venous network in other living bodies such as hand, a toe, etc.

The sensor comprises a set B of infrared emitters E, such as for example light emitting diodes or organic light emitting diodes, an image acquisition means C, such as a CCD camera, positioned facing the set B so that the infrared emitters E illuminate this means C, and image processing means O that are connected to the acquisition means C so as firstly to obtain an image acquired by the means C and secondly to reveal in this image the venous network V of the finger CV by applying a processing to the acquired image such as for example the one described in the introductory part.

According to one feature of the present invention, at least one presence detector DP is associated with each infrared emitter E in the set B. The function of this presence detector DP is to determine whether a part of the finger is present between this infrared emitter and the means C.

Several types of presence detector of the prior art can be used. The constraint imposed is that they must give a binary indication relating to the presence or not of the part of the finger CV.

According to one embodiment, at least one of the presence detectors DP associated with at least one infrared emitter E in the set B is an ultrasonic sensor. Ultrasonic sensors, also called ultrasonic telemeters, form part of the class of sensors that make it possible to measure distances without contact. The ultrasonic telemeter is based on the measurement of the time elapsed between the emission of an ultrasonic wave and the reception of an echo. More precisely, when the ultrasonic wave is emitted, it propagates at the speed of sound, in the surrounding air, at 342 m/sec. As soon as an obstacle is encountered, the echo returns to the transducer of the telemeter, which then calculates the time elapsed between the emission and reception of the wave and derives therefrom the distance between it and the obstacle. Thus, in the absence of part of the finger CV, the ultrasonic sensor determines a first distance between it and an obstacle such as for example the acquisition means C or a support on which the venous network sensor is placed and, when part of the finger CV is situated close to an ultrasonic sensor, another distance is determined. The presence of a part of the finger is then detected if this other distance is less than the first distance.

According to another embodiment, at least one of the presence detectors associated with at least one infrared emitter E in the set B is an infrared detector. This type of detector detects the movement of a body the temperature of which is close to the human body, in this case part of the finger CV.

According to another embodiment, at least one of the presence detectors associated with at least one infrared emitter E in the set B is a laser telemeter.

According to another embodiment, at least one of the presence detectors DP associated with at least one infrared emitter E of the set E is a switch reacting to a light flux, such as for example a photodiode or a phototransistor. A photodiode or phototransistor remains in an "open" state as long as it is not illuminated by a light flux and switches to a "closed" state as soon as it is illuminated.

It should be noted that the present invention is not dependent on the exclusive use of one or other of the above presence detectors DP. Several types of presence detector can be associated with the same infrared emitter and/or the same type of presence detector can be associated with the said infrared emitter and/or the type of presence detector differs from one infrared emitter to another.

The number of presence detectors per infrared emitter and the relative positionings thereof around the same infrared emitter are two parameters that determine the logic for detecting the presence of a part of the finger between this infrared emitter and the means C.

FIGS. 2a-2d present various examples of associations of presence detectors with an infrared emitter.

A single presence detector DP may be associated with an infrared emitter (FIG. 2a).

This presence detector DP can be integrated in the infrared emitter.

This presence detector DP may also be positioned around the infrared emitter, for example at any one of the cardinal points of the infrared emitter, that is to say at the top, bottom, left or right.

There is no particular logic in the last two cases since the presence detector DP directly indicates the presence of a part of the finger.

Two presence detectors DP1 and DP2 may be associated with the same infrared emitter E. These two presence detectors may be aligned, as illustrated in FIG. 2b, or form a particular angle between them, as illustrated in FIG. 2c. The protection logic can then be either to consider that the finger is present as soon as one of the two presence detectors DP1 or DP2 indicates this presence, or to consider it only if the two presence detectors DP1 and DP2 so indicate.

More than two presence detectors DP may be associated with the same infrared emitter E and a particular detection logic can be considered without however departing from the scope of the present invention.

According to a preferred embodiment illustrated in FIG. 2d, four presence detectors DP1, . . . , DP4 are associated with an infrared emitter E. Each of these four presence detectors is positioned at a cardinal point of the infrared emitter. The detection logic can then be to consider that the finger is present either as soon as one of the four presence detectors indicates the presence of a part of the finger or as soon as two of the four presence detectors so indicate, or as soon as three of the four presence detectors so indicate, or only when the four presence detectors so indicate.

The set B of infrared emitters comprises several infrared emitters E that can be positioned with respect to one another in a particular way without for all that departing from the scope of the present invention.

According to one embodiment illustrated by FIG. 3, the infrared emitters Ei,j (i=1 to L and j=1 to C) are positioned on L rows and C columns so as to form a matrix of L rows and C columns. It is understood from this that C or L may be equal to unity. An array is then spoken of. According to the example in FIG. 3, the set B comprises two rows and four columns and four presence detectors, denoted 1, 2, 3 and 4, are associated with each infrared emitter Ei,j.

The dimensions of the set B in FIG. 3 are large because of the large number of presence detectors. It is then advantageous to alternate by row and/or column an infrared emitter Ei,j and a presence detector. The number of presence detectors is thus reduced, which gives rise firstly to a reduction in the manufacturing cost of the set B and secondly a reduction in the dimensions thereof.

According to the example in FIG. 4a, this alternation is made on each row and each column. Thus, the presence detectors marked 1 and respectively 2 are associated with two infrared emitters in two consecutive columns and the same row, or respectively two consecutive rows and the same column. The other presence detectors (without any mark in FIG. 4a) are associated with a single infrared emitter.

According to the preferred mode in FIG. 4b, this alternation is also made on each row and each column but the presence detectors marked 1 are this time associated with three infrared emitters. The other presence detectors (without any mark in FIG. 4b) are associated with a single infrared emitter.

This preferred embodiment optimises the dimensions of the set B.

The preferred detection logic, which is implemented for the set B described in relation to FIG. 3, 4a or 4b, is to then consider the presence of a part of the finger CV between an infrared emitter and the means C when the four presence detectors DP that are associated with it indicate the presence of a part of the finger. This detection logic ensures that the infrared emitter, when it is activated, will not directly illuminate the means C even partially.

Other embodiments are of course possible, by carrying out this alternation solely on the rows or columns or on certain rows and/or certain columns.

Returning to FIG. 1, according to another feature, the venous network sensor also comprises a device D for slaving the activation of the infrared emitters E to the presence of the finger CV between the set B and the means C. The device D comprises means MDP for checking whether one of the presence detectors DP indicates the presence of a part of a living body, in this case a finger. The device D also comprises means MC for activating an infrared emitter E in the set B using a detection logic which, as explained in relation to FIGS. 2a-2d, 3 and 4, depends on the number of presence detectors DP associated with each infrared emitter E and the relative positionings thereof around the same infrared emitter.

The means MDP and MC may, for example, be implemented by an electronic circuit that may be formed from logic gates and/or include a microprocessor or a microcontroller.

According to one embodiment of the device D relating to the case where at least one of the presence detectors DP is a switch reacting to a light flux, the device D comprises a single light source S that is designed to illuminate said at least one presence detector DP.

According to one embodiment, the light source S is formed by at least one of the infrared emitters E in the set B.

According to one embodiment of the device, the source S is positioned so that the light beam thereof, shown in bold lines in FIG. 5, illuminates the region where the finger CV is liable to be situated. Thus, when the finger CV is present in this region (or part of this finger), the light beam is reflected on this finger and illuminates the presence detector or detectors DP (photodiodes or phototransistors) associated with each infrared emitter when a part of the finger is situated between this infrared emitter and the means C. According to the example in FIG. 5, all the presence detectors are illuminated except the one or ones associated with the infrared emitter denoted E.

According to another embodiment of the device, the source S is positioned so as to illuminate the presence detectors DP (photodiodes or phototransistors) when the finger is absent and to no longer illuminate the presence detectors DP when part of the finger is present between the infrared emitters that are associated with these presence detectors DP and the means C, as illustrated in FIG. 6. According to this example, only the presence detector or detectors DP associated with the infrared transmitter E are still illuminated in the presence of the finger CV.

Thus, in general terms, the device D uses a method for slaving the activation of a set of infrared emitters E to the presence of a living body, in this case a finger, between this set and the means C.

During this method, the state of each presence detector DP is checked. When one of these presence detectors DP indicates the presence of a part of a living body, in this case of a finger, each infrared emitter Ei,j is activated if the presence of a part of the finger is detected by at least one presence detector DP that is associated therewith and each infrared emitter Ei,j is deactivated as long as the presence of a part of the finger is not detected.

According to one embodiment of the device relating to the case where a single presence detector DP is associated with each infrared emitter Ei,j, the infrared emitter Ei,j is activated if the presence of a part of the finger is detected by this presence sensor DP and this emitter Ei,j is deactivated as long as the presence of a part of the finger is not detected by the presence detector DP.

According to the preferred embodiment of the device relating to the case where several presence detectors DP are associated with each infrared emitter Ei,j, such as for example a case described in relation to one of FIG. 3, 4a or 4b, as soon as one of the presence detectors DP indicates the presence of part of a finger, for example the right-hand detector of the infrared emitter E1,4, the method is on standby until other presence detectors DP indicate the presence of this finger. When the four presence detectors DP associated with infrared emitter E1,4 indicate simultaneously the presence of the finger, the infrared emitter E,1,4 is activated and an image of the finger can then be acquired by the means C. The same applies to the activation of the other infrared emitters of the set B. As soon as one of these four detectors no longer indicates the presence of the finger, the infrared emitter E,1,4 is deactivated.

Thus, as soon as an infrared emitter of the set B is activated, an image of the finger can be acquired.

In the case where the light source S is formed by at least one infrared emitter E of the set B or when this light source S is an infrared emitter, the state of activation/deactivation of the infrared emitters of the set B remains constant throughout the whole of the integration of the means C, that is to say during the acquisition of an image by the means C. This in order to obtain a usable image for extraction of the venous network of the finger.

Whatever the case, it will be understood that the slaving method according to the present invention is very rapid compared with that of the prior art. It is consequently highly advantageous as it enables the venous network of a living body, such as a finger, to be acquired even if this living body is present between the set of infrared emitters and the means C only for a very short moment.

The invention claimed is:

1. Venous network sensor comprising:
    a set of infrared emitters,
    an acquisition means facing the set of infrared emitters,
    a set of presence detectors, each presence detector being associated with at least one infrared emitter, each infrared emitter being associated with at least one presence detector, each presence detector being intended to detect if a part of a living body is present between the infrared emitter with which the presence detector is associated and the acquisition means,
    means of activating an infrared emitter, when a presence detector associated therewith answers to a specific detection logic indicating the presence of a part of a living body between the associated infrared emitter and the acquisition means, and
    means of deactivating an infrared emitter, when the presence detector associated therewith does not answer to the specific detection logic,
    wherein four presence detectors are associated with each infrared emitter, and wherein each of the four presence detectors is positioned at a cardinal point of each infrared emitter, and the detection logic indicates the presence of the living body either by one, two, three or four of the presence detectors.

2. Venous network sensor according to claim 1, wherein the presence detectors and the infrared emitters are arranged in rows and in columns.

3. Venous network sensor according to claim 2, wherein in each row and in each column, an infrared emitter alternates with a presence detector.

4. Venous network sensor according to claim 1, wherein at least one presence detector in the set is a switch reacting to a light flux, and wherein the venous network sensor comprises also a single light source (S) designed to illuminate said switch.

5. Venous network sensor according to claim 4, wherein the single light source (S) is positioned to illuminate said at least one switch by reflection on a part of the living body.

6. Venous network sensor according to claim 4, wherein the single light source (S) is positioned to illuminate said at least one switch in the absence of a living body.

* * * * *